United States Patent [19]

Griffin, Jr.

[11] 4,153,066

[45] *May 8, 1979

[54] METHOD OF REDUCING FRICTION LOSS

[75] Inventor: Thomas J. Griffin, Jr., Sand Springs, Okla.

[73] Assignee: The Dow Chemical Company, Midland, Mich.

[*] Notice: The portion of the term of this patent subsequent to Jun. 21, 1994, has been disclaimed.

[21] Appl. No.: 816,111

[22] Filed: Jul. 15, 1977

Related U.S. Application Data

[63] Continuation-in-part of Ser. No. 656,675, Feb. 9, 1976, abandoned, and a continuation-in-part of Ser. No. 698,666, Jun. 22, 1976, Pat. No. 4,031,014.

[51] Int. Cl.² .............................................. F17D 1/16
[52] U.S. Cl. .......................................... 137/13; 44/76; 166/308; 252/1; 252/8.55 R; 252/32.5; 252/89 R; 260/980
[58] Field of Search ................. 137/13; 252/1, 8.55 R

[56] References Cited

U.S. PATENT DOCUMENTS 4,031,014  6/1977  Griffin, Jr. ...................... 252/8.55 R

*Primary Examiner*—Leland A. Sebastian
*Attorney, Agent, or Firm*—G. H. Korfhage; Bruce M. Kanuch

[57] ABSTRACT

The reaction product of a hydroxy ether and a pentavalent phosphorus compound with a short chain and/or long chain alcohol can be employed to gel organic liquids by mixing the reaction product with an organic liquid in the presence of certain aluminum activator compounds.

37 Claims, No Drawings

METHOD OF REDUCING FRICTION LOSS

CROSS-REFERENCE TO RELATED APPLICATION

This is a continuation-in-part application of application Ser. No. 656,675, filed Feb. 9, 1976, now abandoned.

Another continuation-in-part application of said Ser. No. 656,675—namely, Ser. No. 698,666, filed June 22, 1976, now U.S. Pat. No. 4,031,014—also relates to a method of reducing friction loss, but has claims differing in scope from those in the present application.

BACKGROUND OF THE INVENTION

This invention relates to improved methods of reducing friction losses, i.e., the friction pressure, of organic based liquids flowing through confining conduits such as in internal combustion engines, fracturing fluids employed to treat subterranean formations, metal working fluids and the like. Representative art relating to these types of compounds, their preparation and use are found in U.S. Pat. Nos. 2,245,649; 2,274,302; 2,329,707; 2,346,155; 2,885,417; 2,905,683; 2,983,678; 2,983,679; 3,010,903; 3,331,896; 3,470,222; 3,494,949; 3,505,374; 3,547,820; 3,575,859; 3,584,087; 3,706,822 and 3,757,864, the teachings of which are specifically incorporated herein by reference.

Other patents made of record in the parent application include U.S. Pat. Nos. 1,944,530; 2,005,619; 3,020,303; 3,133,787; 3,484,474; 3,755,509; 3,757,864; and British Pat. No. 1,415,190, which is equivalent to Canadian Pat. No. 974,539.

Organic phosphoric acid esters have been employed in their free acid form and/or salts thereof as detergents, lubricating liquids, corrosion inhibitors, friction reducing agents, thickening agents and the like.

U.S. Pat. No. 3,757,684 teaches that certain aluminum salts of organic phosphoric acid esters are useful as friction reducing and gelling agents for nonpolar organic liquids. The salts are formed by reacting a basic aluminum compound with an ester which has been formed by reacting one or more monohydric aliphatic alcohols with a phosphorus compound such as $P_2O_5$, phosphorus oxychloride, $PCl_5$, $PF_5$, and the like.

It has now been discovered that certain metal salts of complex reaction products of a hydroxy ether and a phosphorus compound such as $P_2O_5$ are at least as effective as, and in many instances more effective than, the agents disclosed in U.S. Pat. No. 3,757,864 to reduce friction loss of refined oils and certain crude oils flowing through a confining conduit.

SUMMARY OF THE INVENTION

The product employed in the present invention is formed by reacting an essentially anhydrous hydroxy ether of the formula $ROR_1OH$ wherein R is a $C_1$ to $C_6$ alkyl group, $R_1$ is a $C_2$ or $C_3$ alkylene group and the total carbon atoms of $R_1$ and R range from 3 to about 8 with a pentavalent phosphorus compound which is substantially free from acid groups such as Cl, F and the like. When the total carbon atoms in the hydroxy ether is three or four, there is also reacted with the hydroxy ether and phosphorus compounds a long chain aliphatic monohydric alcohol containing at least five carbon atoms. A short chain aliphatic monohydric alcohol ($C_1$-$C_4$) can also be reacted therewith if desired. When the total carbon atoms in the hydroxy ether is five or more, there is reacted with the hydroxy ether and phosphorus compound either a long chain aliphatic alcohol (at least five carbons) or a short chain aliphatic monohydric alcohol ($C_1$-$C_4$) or a mixture thereof.

The above defined compounds are reacted with a pentavalent phosphorus compound for a period of time ranging from about 1.5 to about 6 hours at a temperature ranging from about 70° to about 90° C. to form the novel complex reaction product employed in the present invention. As more fully described hereinafter, reaction products having different selected characteristics can be prepared by reacting specific reactants and by varying the order in which they are reacted together.

As a friction reducing agent the reaction product is dispersed into an organic liquid along with an aluminum activator compound such as an alkali metal aluminate, e.g., sodium aluminate, aluminum isopropoxide, hydrated alumina, and the like, the reaction product and the activator being employed in amounts and a specific ratio to each other to impart to the organic liquid a desired reduction in friction loss.

The gelled organic liquid can be employed as a fracturing fluid, as a carrying liquid for solids, and other utilities where organic liquids having favorable flow characteristics, i.e., reduction in friction loss, is useful.

DETAILED DESCRIPTION OF THE INVENTION

The terms "short chain aliphatic monohydric alcohol" and "long chain aliphatic monohydric alcohol" as used herein, while differing from one another in length, each correspond to the formula (Aliph)OH, where each "Aliph" independently represents a substantially unsubstituted aliphatic hydrocarbon moiety. By "substantially" unsubstituted, it is intended to include within the alcohol term, compounds having a minor degree of substitution on the hydrocarbon chain wherein the solubility of the alcohol in nonpolar solvents is not significantly adversely affected, and wherein the nature of the substituent is such, e.g., a halogen, that the carbon chain is not interrupted by heterogenous atoms (e.g., N,O) and the predominate character of the compound is still that of a monohydric alcohol, i.e., so that the single hydroxyl group continues to be the predominate reactive group. Thus, the alcohol terms are not to be construed as embracing the hydroxy ether compounds employed as a separate component in the present invention. Preferably, however, "Aliph" represents a completely unsubstituted aliphatic hydrocarbon moiety, and where such meaning is hereinafter intended, the word "unsubstituted" is used, unmodified by the word "substantially".

The short chain aliphatic monohydric alcohol can be branched or straight chained, primary, secondary, or tertiary and may contain olefinic or acetylenic unsaturation but preferably is saturated. The preferred short chain alcohols are primary, straight chained, unsubstituted, saturated alcohols. One or more can be employed. Specific alcohols which can be employed include, for example, methanol, ethanol, isopropyl alcohol, n-butyl alcohol, sec-butyl alcohol, tert-butyl alcohol and various mixtures thereof. Ethanol and methanol are preferred.

The long chain aliphatic monohydric alcohol can be saturated or olefinically or acetylenically unsaturated, branched or straight chained, and can be a primary, secondary, or tertiary alcohol. The alcohol contains at least 5 carbon atoms and preferably from 5 to about 12 carbon atoms. Examples of suitable alcohols include hexanol, decanol, oleyl alcohol, isooctyl alcohol, dodecanol, 4-decanol, triethylcarbinol, 3-ethyl-3-hexanol, 4-ethyl-3-hexanol and other similar alcohols. Mixtures of various alcohols are also suitable such as certain commercially available mixtures like, for example, AlFOL 810, AlFOL 610 and AlFOL 1012 from Continental Oil Company. The number indicates a mixture of alcohols containing from the lowest to highest number of carbon atoms. For example, AlFOL 810 is a mixture of saturated aliphatic alcohols containing $C_8$ and $C_{10}$ carbon atoms.

Suitable hydroxy ethers which can be employed include, for example, ethylene glycol monomethyl ether, ethylene glycol monoethyl ether, ethylene glycol mono-n-butyl ether, ethylene glycol mono-n-hexyl ether, ethylene glycol monoisobutyl ether, propylene glycol monoethyl ether, propylene glycol monoisobutyl ether, propylene glycol monomethyl ether, mixtures thereof and other like compounds.

The pentavalent phosphorus compound includes, for example, $P_2O_5$ and the like. $P_2O_5$ is preferred. A portion of the $P_2O_5$ may be replaced with a polyphosphoric acid solution; however, in the latter case polyphosphoric acid solutions containing an equivalent of at least about 83 percent by weight $P_2O_5$ are preferred. A maximum substitution of up to about 15 percent, preferably only up to about 10 percent by weight, of the $P_2O_5$ is possible since it is preferred that the reaction be conducted under essentially anhydrous conditions.

The order of addition of the reactants has not been found critical. One method comprises mixing the alcohols and hydroxy ether together and then slowly adding the phosphorus compound thereto with cooling of the reaction mixture to maintain the temperature below about 70° C. After complete addition of the phosphorus compound the temperature of the reaction mixture is maintained at between 70° and 90° C., preferably 80° to 90° C., for from about 1.5 to about 6, preferably from about 1.5 to about 3 hours, but in any event for a sufficient time for the reaction to go to the desired degree of completion. These temperatures are for a reaction conducted at atmospheric pressures. The reaction mixture can be employed as is or as a concentrate in an organic liquid or freeze point depressant, such as an aromatic hydrocarbon or the like.

It has also been discovered that in certain cases when one of the reactants is a short chain alcohol, e.g., methanol or ethanol, reaction products having superior gelling properties can be prepared by adding the phosphorus compound to only a hydroxy ether, and if employed a long chain alcohol followed by a short reaction period of from about 5 to 30 minutes at a reaction temperature of from about 70° to 90° C., then cooling the reaction mixture to below about 70° C., preferably to about 50° C., and then adding the short chain alcohol and continuing the reaction until completion at a temperature of from about 70° to about 90° C., preferably from about 80° to about 90° C.

Where only the hydroxy ether and a short chain alcohol are employed as reactants it is especially preferred to first react the hydroxy ether with the phosphorus compound and then add the short chain alcohol. The separate addition technique is also most preferred when the short chain alcohol is methanol.

The reactants should be reacted together in certain molar ratios to provide reaction products having the most favorable gelling characteristics. The molar ratios which are operable are set forth in the following table wherein $P_2O_5$ is the pentavalent phosphorus compound. Where a mixture of $P_2O_5$ and polyphosphoric acid is employed, the ratios set forth below are based on the total of the moles of $P_2O_5$ provided by the $P_2O_5$ component plus the equivalent moles of $P_2O_5$ provided by the polyphosphoric acid component.

| Mole Ratio to total $P_2O_5$ (or $P_2O_5$ equivalent) | Reactants | | |
|---|---|---|---|
| | Short Chain Alcohol | $ROR_1OH$ | Long Chain Alcohol |
| Operable | 0 to 5.0 | 0.4 to 4.5 | 0 to 4.0 |
| Preferred | 0.9 to 2.0 | 0.8 to 1.8 | 0 to 1.4 |

The mole ratio of the total of the short chain and/or long chain alcohol and the hydroxy ether to total phosphorous pentoxide ranges from about 2.8:1 to about 7.0:1 with the most preferred ratio being about 3.64:1.

The reaction product is a complex mixture of phosphate esters the exact identity of which has not been determined. It has, however, been found that reaction products produced in an essentially identical manner will have essentially identical gelling properties.

Organic liquids which can be employed in the practice of the present invention are generally nonpolar and include, for example, aliphatic hydrocarbons, halogenated, e.g., chlorinated, hydrocarbons, and mixtures thereof. Preferred aliphatic hydrocarbons include refined paraffinic oils, such as lubricating oils, kerosene, diesel oil, fuel oil and the like. Certain crude oils are also suitable. The effectiveness and optimum quantities of reaction product to reduce the friction loss of any particular organic liquid should be ascertained prior to a large scale use. Since crude oils may vary almost infinitely in composition, small scale tests are particularly advisable when crude oil is to be employed. Of the crude oils, those having an API gravity of above about 25 are generally preferred, i.e., the lighter crude oils.

The reaction product is mixed with the organic liquid along with an aluminum activator compound such as an alkali metal aluminate, e.g., sodium aluminate, aluminum isopropoxide (also known as aluminum isopropylate), hydrated alumina, and the like. Sodium aluminate is preferred.

The reaction product and activator are employed in a total amount and weight ratio to each other to produce a product having the desired friction loss characteristics. These amounts and ratios will vary and are dependent on the reactants which are employed to make the reaction product, the exact activator, the organic liquid employed, and the desired degree of friction reduction. For example, less than about 8 gallons of the phosphate ester are employed per 1000 gallons of organic liquid with from about 0.01 to about 1.5 gallons of a 38 percent by weight of a sodium aluminate solution per 1000 gallons of organic liquid. For different quantities of phosphate ester the amount of metal salt will vary proportionally.

When the reaction product is employed to decrease the friction loss of an organic liquid which is to be employed as a fracturing fluid standard techniques of mixing and fracturing can be employed. For example, a suitable amount of a reaction product which has been previously prepared is mixed with, for example, kerosene or crude oil in a mixing tank along with a suitable activator. The so prepared fluid is then employed to fracture, for example, a petroleum producing formation employing standard equipment and techniques known in the art. In general, the method comprises pumping the so prepared fluid through a borehole and into contact with the subterranean formation to be fractured at a sufficient pressure to fracture the same. It is preferred to employ a sufficient amount of the reaction product and activator to reduce the friction pressure of the organic liquid flowing through the contemplated confining conduit by at least about 5 percent. Generally from about 0.1 to about 0.9 gallons of reaction product per 1000 gallons of organic liquid is suitable.

Various reaction products suitable for use in the practice of the invention were prepared in the following manner:

Preparation of Alkyl Phosphates by Mixed Addition

The desired quantities of alcohol and hydroxy ether were placed in a reaction flask equipped with a mechanical stirrer, reflux condenser, thermometer and heating mantle. With continuous stirring, $P_2O_5$ was added, maintaining the temperatures below 70° C. with cooling. After complete addition of $P_2O_5$, the mixture was heated to 80° C. and maintained for six hours. The product was then cooled, and formulated as described hereinafter.

Preparation of Alkyl Phosphates by Separate Addition

The procedure described directly hereinbefore was followed, except that the $P_2O_5$ was first added to the hydroxy ether, and if employed, a long-chain alcohol. After complete addition of the $P_2O_5$ and 15 minutes of mixing, the short-chain alcohol (methanol and/or ethanol) was added while the temperature of the reaction mixture was maintained below 50° C. by controlled addition. The mixture was then heated to 80° C. and reacted for six hours. The product was then cooled, and formulated as described hereinafter.

Preparation of Alkyl Phosphate Esters Employing Polyphosphorous Acid

The first procedure described above was followed except that after two hours at 80° C., the mixture was cooled to 50° C. and a certain amount of polyphosphoric acid was added. The mixture was then heated to 80° C. for an additional 3½ hours.

What is claimed is:

1. A method of reducing the friction loss generated by an organic liquid selected from the group consisting of aliphatic hydrocarbons, aliphatic halogenated hydrocarbons, and crude oil, flowing through a confining conduit, which comprises:

mixing up to about 0.9 gallon per 1000 gallons of said organic liquid of an organic phosphate ester reaction product comprising the reaction of
A. a pentavalent phosphorus compound selected from the group consisting of $P_2O_5$ and a mixture of $P_2O_5$ with polyphosphoric acid;
B. a hydroxy ether of the formula $ROR_1OH$ wherein R is a $C_1$ to $C_6$ alkyl group, $R_1$ is a $C_2$ or $C_3$ alkylene group and the total carbon atoms of R and $R_1$ range from 3 to about 8; and
C. when the total carbon atoms of R and $R_1$ is 3 or 4, a long chain substantially unsubstituted monohydric aliphatic alcohol containing at least 5 carbon atoms, but when the total carbon atoms of R and $R_1$ is 5 to 8, an alcohol selected from the group consisting of a long chain substantially unsubstituted monohydric aliphatic alcohol containing at least 5 carbon atoms, a short chain substantially unsubstituted monohydric aliphatic alcohol containing from 1 to 4 carbon atoms and a mixture of said alcohols, the individual mole ratios of the hydroxy ether, the long chain alcohol and the short chain alcohol to total $P_2O_5$ being within the ranges of 0.4:1 to 4.5:1; 0:1 to 4.0:1 and 0:1 to 5.0:1 respectively, said reaction being conducted at temperature ranging from about 70° to about 90° C. for a period of time of from about 1.5 to about 6 hours, and, a sufficient quantity of an aluminum activator compound to provide friction reduction, said aluminum compound being selected from the group consisting of an alkali metal aluminate, aluminum isopropoxide, and hydrated alumina.

2. The method of claim 1 wherein the total mole ratio of the hydroxy ether, the long chain alcohol and the short chain alcohol to total $P_2O_5$ is about 3.64 to 1.

3. The method of claim 1 wherein the reaction temperature ranges from about 80° to about 90° C. and the reaction time ranges from about 1.5 to about 3 hours.

4. The method of claim 1 wherein the pentavalent phosphorus compound is $P_2O_5$.

5. The method of claim 1 wherein the aluminum compound is sodium aluminate.

6. The method of claim 1 wherein the organic liquid is an aliphatic hydrocarbon.

7. The method of claim 1 wherein each alcohol is unsubstituted.

8. The method of claim 7 wherein the aluminum compound is sodium aluminate.

9. The method of claim 7 wherein the individual mole ratios of the hydroxy ether, the long chain alcohol and the short chain alcohol to $P_2O_5$ are within the ranges of 0.8:1 to 1.8:1; 0:1 to 1.4:1; and 0.9:1 to 2.0:1 respectively.

10. The method of claim 9 wherein the total mole ratio of the hydroxy ether, the long chain alcohol and the short chain alcohol to total $P_2O_5$ ranges from about 2.8:1 to about 7.0:1.

11. The method of claim 1 wherein when the total carbon atoms of R and $R_1$ is 3 or 4 there is also reacted a short chain substantially unsubstituted monohydric aliphatic alcohol containing from 1 to 4 carbon atoms or a mixture of said alcohols.

12. The method of claim 11 wherein the long chain alcohol is unsubstituted and contains from 5 to 12 carbon atoms, and wherein the short chain alcohol is methanol, ethanol, or a mixture thereof.

13. The method of claim 11 wherein the aluminum compound is sodium aluminate.

14. The method of claim 13 wherein the organic liquid is an aliphatic hydrocarbon.

15. The method of claim 1 wherein the long chain monohydric alcohol contains from 5 to about 12 carbon atoms.

16. The method of claim 15 wherein the short chain alcohol is a primary, unsubstituted, straight chain, saturated alcohol.

17. The method of claim 16 wherein the short chain alcohol is ethanol, methanol, or a mixture thereof, and the long chain alcohol is unsubstituted.

18. The method of claim 17 wherein the short chain alcohol is methanol.

19. The method of claim 17 wherein the reaction product is employed in an amount of from about 0.1 to about 0.9 gallons per 1000 gallons of organic liquid.

20. A method of reducing the friction loss generated by an organic liquid selected from the group consisting of aliphatic hydrocarbons, aliphatic halogenated hydrocarbons, and crude oil, flowing through a confining conduit, which comprises:

mixing up to about 0.9 gallon per 1000 gallons of said organic liquid of an organic phosphate ester reaction product comprising the reaction of A. a pentavalent phosphorus compound, selected from the group consisting of $P_2O_5$ and a mixture of $P_2O_5$ with polyphosphoric acid;

B. a hydroxy ether of the formula $ROR_1OH$ wherein R is a $C_1$ to $C_6$ alkyl group, $R_1$ is a $C_2$ or $C_3$ alkylene group and the total carbon atoms of R and $R_1$ range from 3 to about 8; and C. when the total carbon atoms of R and $R_1$ is 3 or 4 a long chain substantially unsubstituted monohydric aliphatic alcohol containing at least 5 carbon atoms and a short chain substantially unsubstituted monohydric aliphatic alcohol containing from one to four carbon atoms; when the total carbon atoms of R and $R_1$ is five to eight a short chain substantially unsubstituted monohydric aliphatic alcohol containing from one to four carbon atoms;

the individual mole ratios of the hydroxy ether, the long chain alcohol and the short chain alcohol to total $P_2O_5$ being within the ranges of 0.4:1 to 4.5:1; 0:1 to 4.0:1 and 0:1 to 5:1 respectively, and the total mole ratio of said three components to total $P_2O_5$ being from about 2.8:1 to about 7.0:1, said reaction being conducted by first reacting the phosphorus compound with the hydroxy ether, and when the total carbon atoms of R and $R_1$ is 3 or 4, also with the long chain alcohol for a period of time of from about 5 to about 30 minutes at a temperature of from about 70° to about 90° C., cooling the reaction mixture to below 70° C., adding the short chain alcohol to the reaction mixture and reacting the mixture at a temperature of from about 70° to about 90° C. for a period of time to provide a total reaction time of from about 1.5 to about 6 hours, and, a sufficient quantity of an aluminum activator compound to provide friction reduction, said aluminum compound being selected from the group consisting of an alkali metal aluminate, aluminum isopropoxide, and hydrated alumina.

21. The method of claim 20 wherein when the total carbon atoms of R and $R_1$ is five to eight there is also reacted with the pentavalent phosphorus compound and the hydroxy ether a long chain monohydric alcohol containing at least 5 carbon atoms prior to reacting the short chain alcohol.

22. The method of claim 20 wherein the long chain alcohol has 5 to 12 carbon atoms.

23. The method of claim 20 wherein the pentavalent phosphorus compound is $P_2O_5$.

24. The method of claim 20 wherein the short chain alcohol is a primary, unsubstituted, straight chain, saturated alcohol.

25. The method of claim 24 wherein the short chain alcohol is ethanol, methanol, or a mixture thereof, and the long chain alcohol is unsubstituted.

26. The method of claim 25 wherein the short chain alcohol is methanol.

27. The method of claim 25 wherein the short chain alcohol is ethanol.

28. The method of claim 20 wherein each alcohol is unsubstituted.

29. The method of claim 28 wherein the long chain alcohol has 5 to 12 carbon atoms; the pentavalent phosphorus compound is $P_2O_5$; and the short chain alcohol is primary, straight chain, and saturated.

30. The method of claim 29 wherein the aluminum compound is sodium aluminate.

31. The method of claim 30 wherein the organic liquid is an aliphatic hydrocarbon.

32. The method of claim 31 wherein from about 0.1 to about 0.9 gallon of the reaction product is employed per 1000 gallons of organic liquid.

33. The method of claim 29 wherein said hydroxy ether is selected from the group consisting of ethylene glycol monomethyl ether, ethylene glycol monoethyl ether, ethylene glycol mono-n-butyl ether, ethylene glycol mono-n-hexyl ether, ethylene glycol monoisobutyl ether, propylene glycol monomethyl ether, propylene glycol monoisobutyl ether, propylene glycol monomethyl ether and mixtures thereof.

34. The method of claim 33 wherein the individual mole ratios of the hydroxy ether, the long chain alcohol and the short chain alcohol to $P_2O_5$ are within the ranges of 0.8:1 to 1.8:1; 0:1 to 1.4:1; and 0.9:1; to 2.0:1 respectively.

35. The method of claim 34 wherein the short chain alcohol is methanol, ethanol, or a mixture thereof.

36. The method of claim 35 wherein the total mole ratio of the short chain alcohol, hydroxy ether and long chain alcohol to $P_2O_5$ is about 3.64:1.

37. The method of claim 36 wherein the short chain alcohol is methanol.

* * * * *